(12) United States Patent
Sode

(10) Patent No.: US 7,232,861 B2
(45) Date of Patent: Jun. 19, 2007

(54) ENZYME-MIMICKING POLYMERS

(76) Inventor: Koji Sode, 13-16, Minami 1-chome, Meguro-ku, Tokyo 152-0013 (JP)

( * ) Notice: Subject to any disclaimer, the term of this patent is extended or adjusted under 35 U.S.C. 154(b) by 445 days.

(21) Appl. No.: 10/380,220

(22) PCT Filed: Sep. 10, 2001

(86) PCT No.: PCT/JP01/07835

§ 371 (c)(1),
(2), (4) Date: Mar. 12, 2003

(87) PCT Pub. No.: WO02/22698

PCT Pub. Date: Mar. 21, 2002

(65) Prior Publication Data

US 2003/0186330 A1 Oct. 2, 2003

(30) Foreign Application Priority Data

Sep. 12, 2000 (JP) .............................. 2000-318618

(51) Int. Cl.
C08G 63/91 (2006.01)
G01N 33/53 (2006.01)
C08F 30/06 (2006.01)

(52) U.S. Cl. ...................... 525/54.2; 435/7.1; 526/239
(58) Field of Classification Search ................ 526/239; 525/54.2; 435/7.1
See application file for complete search history.

(56) References Cited

U.S. PATENT DOCUMENTS

| 5,370,990 | A |   | 12/1994 | Staniford et al. |
| 5,789,221 | A |   | 8/1998  | Kato et al. |
| 5,972,671 | A |   | 10/1999 | Kato et al. |
| 5,994,110 | A | * | 11/1999 | Mosbach et al. ......... 435/173.1 |
| 6,177,513 | B1 |  | 1/2001  | Takeuchi et al. |
| 2002/0172992 | A1 | * | 11/2002 | Heller .......................... 435/25 |

FOREIGN PATENT DOCUMENTS

| EP | 953358 A | 11/1999 |
| JP | 59-223706 A | 12/1984 |
| JP | 64-33111 A | 3/1989 |
| JP | 5-93019 A | 4/1993 |
| JP | 11-322586 A | 11/1999 |
| JP | 2000-74900 A | 3/2000 |
| JP | 2000-270855 A | 10/2000 |

OTHER PUBLICATIONS

Takeuchi et al. Molecular Imprinting: An Approach to "Tailor-Made" Synthetic Polymers With Biomimetic Functions; Acta Polymer. vol. 47 (1996) pp. 471-480.*

Tsugawa et al. Development of an Enzyme Sensor Utilizing a Novel Fructosyl Amine Oxidase From a Marine Yeast; Electrochemistry, vol. 68, No. 11 (2000) pp. 869-871.*

Kempe et al. Chiral Separation Using Molecularly Imprinted Heteroaromatic Polymers; Journal of Molecular Recognition, vol. 6 (1993) pp. 25-29.*

Sode et al. A New Concept for the Construction of an Artificial Dehydrogenase for Fructosylamine Compounds and its Application for an Amperometric Fructosylamine Sensor; Analytica Chimica Acta, vol. 435 (2001) pp. 151-156.*

Patent Abstract of JP 61-268178, Nov. 27, 1986.
Patent Abstract of JP 61-280297, Dec. 10, 1986.
Patent Abstract of JP 03-155780, Jul. 3, 1991.
Patent Abstract of JP 07-289253, Nov. 7, 1995.
Patent Abstract of JP 08-154672, Jun. 18, 1996.

Motoko Takahashi et al., "Isolation, Purification, and Characterization of Amadoriase . . . ", The Journal of Biological Chemistry, vol. 272, No. 6, Issue of Feb. 7, pp. 3437-3443, 1997.

Amit K. Saxena et al., "Purification and Characterization of a Membrane-bound Deglycating . . . ", The Journal of Biological Chemistry, vol. 271, No. 51, Issue of Dec. 20, pp. 32803-32809, 1996.

Chiara Gerhardinger et al., "Novel Degradation Pathway of Glycated Amino Acids . . . ", The Journal of Biological Chemistry, vol. 279, No. 1, Issue of Jan. 6, p. 218-224, 1995.

Chiara Gerhardinger et al., "Isolation, Purification, and Characterization of an Amadori Product . . . ", The Journal of Biological Chemistry, vol. 269, No. 44, Issue of Nov. 4, pp. 27297-27302, 1994.

Nobuyuki Yoshida et al., "Distribution and Properties of Fructosyl . . . ", Applied and Environmental Microbiology, vol. 61, No. 12, Dec. 1995, pp. 4487-4489.

Tatsuo Horiuchi et al., "Purification and Properties of Fructosylamine Oxidase from Aspergillus sp. 1005", Agric. Biol. Chem., vol. 55, No 2, pp. 333-338, 1991.

Tatsuo Horiuchi et al., "Purification and Properties of Fructosyl-amino Acid . . . ", Agric. Biol. Chem., vol. 53, No. 1, pp. 103-110, 1989.

Yasuyoshi Sakai et al., "Purification and Properties of Fructosyl Lysine Oxidase from Fusarium oxysporum S-1F4", Biosci. Biotech. Biochem., vol. 59, No. 3, pp. 487-491, 1995.

* cited by examiner

Primary Examiner—Jon Weber
Assistant Examiner—Paul Martin
(74) Attorney, Agent, or Firm—Birch, Stewart, Kolasch & Birch, LLP

(57) ABSTRACT

The present invention provides synthetic polymers having novel catalytic functions which mimic enzymatic reactions. The invention also provides a method for measuring glycated proteins such as glycated hemoglobin (HbA1c) and glycated albumin and for measuring their decomposition products fructosylamines, such as fructosylvaline, as well as assay reagents and sensors for use in the method.

2 Claims, 8 Drawing Sheets

Table 1

| Substrate | MIP [nA/mM] | CP [nA/mM] | MIP/CP |
|---|---|---|---|
| Fru-Val | 142 | 82 | 1.8 |
| Fru-Ala | 64 | 39 | 1.6 |
| Fru-Gly | 74 | 32 | 2.3 |
| Fru-Phe | 40 | 31 | 1.3 |
| ε-Fru-Lys | 82 | 76 | 1.1 |

Fru-Val

Fru-Ala

Fru-Gly

Fru-Phe

ε-Fru-Lys

ENZYME-MIMICKING POLYMERS

This application is a 371 of PCT/JP01/07835, filed Sep. 10, 2001.

TECHNICAL FIELD

The present invention relates to synthetic polymers having novel catalytic functions which mimic enzymatic reactions and to novel methods for measuring glycated proteins using the synthetic polymers. More specifically, it relates to polymers obtained by polymerizing a monomer having a catalytic function and a monomer having a molecular-recognition function in the presence of a molecule to be assayed as a template. In addition, it relates to methods for measuring glycated hemoglobin (HbA1c), glycated albumin, and fructosylvaline and other fructosylamines which are the decomposition products of these proteins, as well as assay reagents and sensors for use in these methods. The glycated proteins are used in the fields of, for example, clinical laboratory tests as markers for diagnosis of diabetes mellitus.

BACKGROUND ART

Amino groups in the backbone and side chains of a protein can be non-enzymatically bound to a reducing end-group of a reducing sugar, such as glucose, to form an amadori compound, i.e. a glycated protein. In the blood, hemoglobin is glycated to form glycated hemoglobin (glycohemoglobin; HbA1c). The ratio of HbA1c to hemoglobin in patients with diabetes mellitus is higher than that in healthy persons, and the blood level of HbA1c reflects a blood glucose level over a period of past several weeks. Thus, the blood level of HbA1c is very important in diagnosis of diabetes mellitus and as an indicator of blood glucose level control in patients suffering from diabetes mellitus.

Fructosamine oxidases that act upon amadori compounds have been isolated from various species. It has been suggested that glycated albumin, HbA1c, and other glycated proteins and fructosamines can be assayed by the use of fructosamine oxidase (Japanese Patent Public Disclosure No. 61-268178, No. 61-280297, No. 03-155780, No. 05-192193, No. 07-289253, and No. 08-154672; Agric. Biol. Chem., 53(1), 103–110, 1989; Agric. Biol. Chem., 55(2), 333–338, 1991; J. Biol. Chem., 269(44), 27297–27302, 1994; Appl. Environ. Microbiol., 61(12), 4487–4489, 1995; Biosci. Biotech. Biochem., 59(3), 487–491, 1995; J. Biol. Chem., 270(1), 218–224, 1995; J. Biol. Chem., 271(51), 32803–32809, 1996; J. Biol. Chem., 272(6), 3437–3443, 1997); Electrochemistry, 68(11), 869–871, 2000; and Marine Biotechnology, 3, 126–132, Sep. 5, 2001).

As fructosylamine oxidase is a protein, it is desirable to improve the stability of the enzyme.

DISCLOSURE OF INVENTION

The invention provides a polymer that recognizes an amadori compound and is capable of catalytically oxidizing the compound, as well as to provide a novel method for assaying a glycated protein. More specifically, the present invention provides a method for assaying glycated hemoglobin (HbA1c), glycated albumin, and fructosylamines such as fructosylvaline which is a decomposition product of the glycated proteins, as well as an assay reagent and a sensor for use in the method.

It has now been found that a certain synthetic polymer catalyst can oxidize glycated proteins and decomposition products thereof as a substrate. The polymer can bind to fructosylamine and catalyze its oxidation in the presence of an electron acceptor. Specifically, the present invention provides a synthetic polymer containing imidazole and boronic acid which has a catalytic activity of oxidizing fructosylamines.

The present invention provides a polymer capable of binding to fructosylamine and catalyzing oxidation of the fructosylamine, and a method for assaying fructosylamines and related compounds using the polymer. In another aspect, the present invention provides a method for assaying fructosylamine comprising reacting fructosylamine with a polymer containing imidazole and boronic acid and measuring the amount of an electron acceptor (mediator) reduced by the reaction. Preferably, the reaction is performed in the presence of a mediator, and the pH of the reaction solution is from 6 to 10.

In one aspect, the present invention provides a polymer capable of binding to fructosylamine and catalyzing its oxidation. Preferably, the polymer comprises an imidazole group, or a boronic acid group, or both.

In another aspect, the present invention provides a polymer capable of binding to fructosylamine and catalyzing its oxidation, which is obtained by polymerizing vinylboronic acid.

In another aspect, the present invention provides a polymer capable of binding to fructosylamine and catalyzing its oxidation, which is obtained by synthesizing the polymer using a compound containing a vinylimidazole group.

In another aspect, the present invention provides a polymer capable of binding to fructosylamine and catalyzing its oxidation, which is a copolymer of vinylimidazole and vinylboronic acid.

In another aspect, the present invention provides a polymer capable of binding to fructosylamine and catalyzing its oxidation, which is obtained by synthesizing the polymer using 1-vinylimidazole.

In another aspect, the present invention provides a polymer capable of binding to fructosylamine and catalyzing its oxidation, which is obtained by synthesizing the polymer using 4-vinylphenylboronic acid.

In another aspect, the present invention provides a polymer capable of binding to fructosylamine and catalyzing its oxidation, which is obtained by synthesizing the polymer using a crosslinking reagent. Preferably, the crosslinking reagent is ethylene glycol dimethacrylate (EGDMA).

In another aspect, the present invention provides a polymer capable of binding to fructosylamine and catalyzing its oxidation, which is obtained by synthesizing the polymer in the presence of a template molecule. Preferably the template molecule is removed after polymerization.

In another aspect, the present invention provides a polymer capable of binding to fructosylamine and catalyzing its oxidation, which is obtained by synthesizing the polymer in the presence of fructosylamine as a template molecule. Preferably, fructosylamine is fructosylvaline.

In the above described polymers, it is preferable that the template molecule is methylamine. Preferably, methylamine is methylvaline.

In yet another aspect, the present invention provides a fructosylamine assay kit comprising a polymer capable of binding to fructosylamine and catalyzing its oxidation. The present invention also provides a method for assaying fructosylamine in a sample, comprising electrochemically determining the amount of a reduced mediator formed by oxidation of the fructosylamine.

In another aspect, the present invention provides a fructosylamine sensor for use in the above described assay method. Preferably, the fructosylamine sensor comprisese a carbon paste electrode.

In yet another aspect, the present invention provides a glycated hemoglobin assay kit for use in the above described assay method. The present invention also provides a glycated hemoglobin sensor for use in the above described assay method. The present invention also provides a method for assaying glycated albumin, comprising measuring the amount of glycated albumin or fructosylamine generated by decomposition of the glycated albumin in a sample by the method described above.

In another aspect, the present invention provides a glycated albumin assay kit for use in the above described assay method. The present invention also provides a glycated albumin sensor for use in the above described assay method.

In yet another aspect, the present invention provides a method for preparing a synthetic polymer capable of binding to fructosylamine and catalyzing oxidation of the fructosylamine in the presence of an electron acceptor, wherein said method comprises polymerizing vinylboronic acid. Preferably, the polymer is obtained by copolymerizing vinylimidazole and vinylboronic acid. More preferably, the polymer is obtained by copolymerizing vinylimidazole and 4-vinylphenylboronic acid. The monomer mixture to be polymerized may also contain a crosslinking reagent, a template molecule and/or a basic monomer.

BEST MODE FOR CARRYING OUT THE INVENTION

Figure 1:
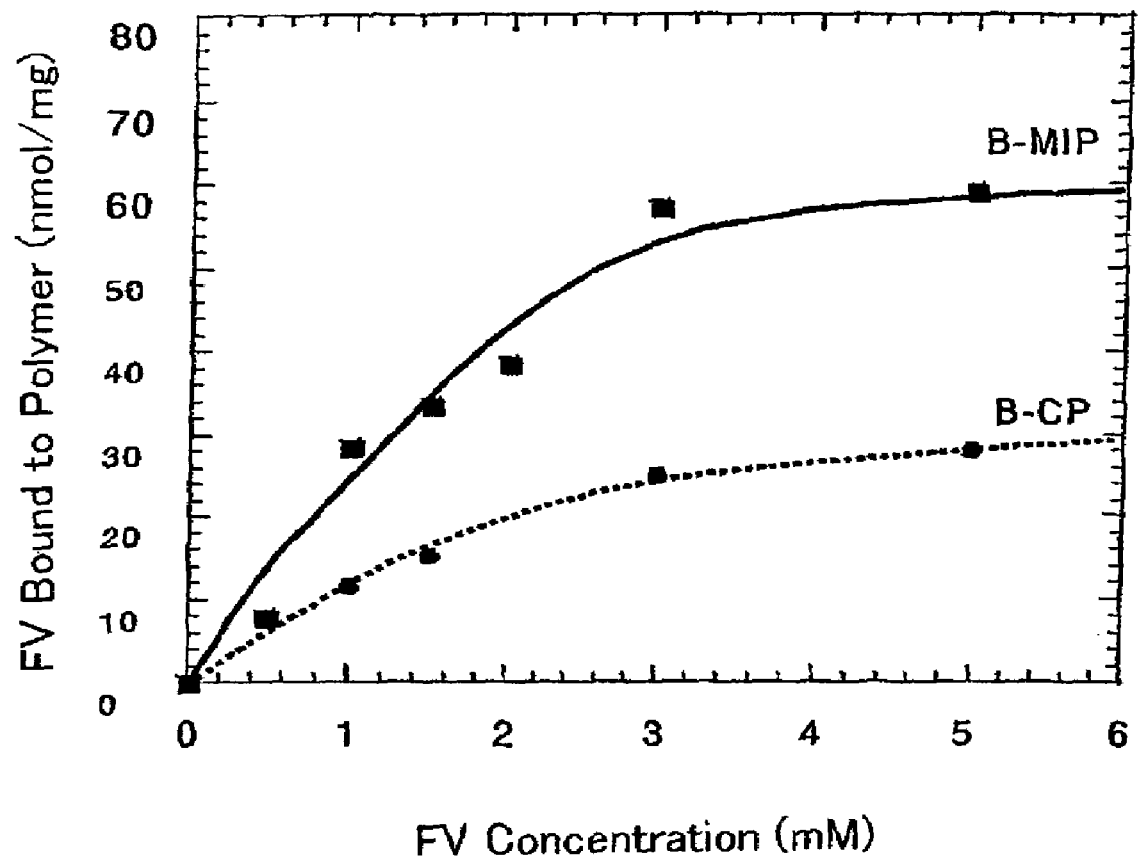
FIG. 1 shows the ability of the polymer synthesized in Example 1 to bind to fructosylvaline; B-MIP represents a boronic acid polymer prepared in the presence of a template molecule; and B-CP represents a boronic acid polymer prepared in the absence of a template molecule.

The polymers of the present invention capable of binding to fructosylamines and catalyzing its oxidation may be a synthetic polymer containing an imidazole group, a boronic acid group, or both. Such polymers having both of imidazole group and boronic acid group can be synthesized by copolymerizing a monomer having an imidazole group and a monomer having a boronic acid group. To synthesize such polymers, 1-vinylimidazole and 4-vinylphenylboronic acid or any other monomers having an imidazole group and a boronic acid group may be used. Any other polymers capable of recognizing fructosylamines and catalyzing oxidation of the fructosylamines in the presence of an electron acceptor can also be used in the present invention. Polymers can also be prepared by polymerization of any monomers having a functional group that can serve as a general base catalyst, for example, bipyridyl containing pyridine. Examples of such a monomer include 4(5)-vinylimidazole, 4-vinylpyridine, 2-vinylpyrazine, 2-vinylpyridine, and 2-vinyl-2, 6-diamino-s-triazine.

The polymer may be a copolymer obtained by polymerizing the above monomers and polymerizable functional monomers such as acrylic acid and acrylamide. Sometimes copolymers comprising basic polymers, such as allylamine, N,N'-dimethylaminoethyl methacrylate, dimethylaminopropyl methacrylate, and diethylaminoethyl methacrylate may have higher selectivity toward fructosylvaline as compared with fructosyllysine even when prepared in the absence of fructosylvaline as a template. By adding, for example, 2-hydroxyethyl methacrylate in the polymerization process, polymers with higher hydrophilicity may be obtained.

In addition, the polymers of the present invention can be stabilized by crosslinking. For example, by adding a crosslinking agent such as EGDMA upon polymerization of the polymers, polymers having more stabilized structures and improved ability of molecular recognition may be obtained.

When a template molecule to be recognized by the polymer is used upon crosslinking, the resulting polymers can exhibit a greater ability of molecular recognition. For example, a radical polymerization reaction can be conducted using 1-vinylimidazole, 4-phenylvinylboronic acid, EGDMA as a crosslinking agent, and fructosylvaline as a fructosylamine. The resulting polymer may has greater ability of molecular recognition 1.2 times or more, and preferably 1.5 times or more than that of a polymer prepared without the use of a template molecule (control polymer). This polymer can bind to fructosylvaline in an amount per unit polymer 1.5 times or more of the control polymer. As a result, the polymer catalyzes oxidation of fructosylvaline in the presence of an electron acceptor at a rate of 1.2 times or more, preferably 1.5 times or more of the control polymer.

According to the present invention, polymers having higher selectivity toward fructosylvaline than other fructosylamines can be obtained by conducting a polymerization reaction in the presence of fructosylvaline as a template. In addition to glycated hemoglobin, glycated proteins in the blood also include glycated albumin. The glycated albumin is derived from albumin, where the amine group at the ε-position of lysine in the amino acid sequence of albumin is glycated. According to conventional glycated albumin assays, glycated hemoglobin and glycated albumin cannot clearly be distinguished from each other. The polymers obtained by synthesizing the polymer in the presence of fructosylvaline as a template have improved reactivity with fructosylvaline than with ε-fructosyl-lysine, a model compound of glycated albumin, and thus can be used to make sensors capable of specifically recognizing glycated hemoglobin over glycated albumin present in the blood.

Methylamine can also be used as a template molecule. For example, a polymer having selectivity toward fructosylvaline can be obtained by preparing a polymer in the presence of methylvaline as a template.

In the methods of the present invention for assaying glycated proteins such as glycated albumin and HbA1c, or assaying fructosylamines, such as fructosylvaline formed by enzymatic or chemical decomposition of glycated albumin and HbA1c, the fructosylamine or other substances are reacted with the polymer of the invention. Preferably, the assay is performed in the presence of a mediator in a reaction solution of pH 6 to 10, more preferably pH 6 to 8 and most preferably around pH 7.

When a polymer is synthesized by polymerizing vinylimidazole and vinylboronic acid using EGDMA as a crosslinking agent in the presence of fructosylvaline, and an assay is performed using the polymer as a catalyst, phenazine methosulfate (PMS) and dichlorophenolindophenol (DCIP) as mediators, and fructosylvaline as a substrate, it is observed that fructosylvaline is oxidized with time whereas DCIP is reduced and discolored by the mediation of PMS. The concentration of fructosylvaline can be determined based on the rate of discoloring of DCIP as an indicator. Specifically, fructosylvaline of unknown concentration can be quantified with a sensitivity of less than or equal to 1 mM by using the polymer of the present invention as a catalyst and phenazine methosulfate (PMS) and dichlorophenolindophenol (DCIP) as mediators.

Various artificial electron mediators can also be used. Such mediators include, for example, potassium ferricyanide, ferrocene, and osmium derivatives.

Assay Kits

In another aspect, the present invention provides a kit for assaying HbA1c, glycated albumin, and other glycated proteins and fructosylamines for use in the assay methods of the present invention. The glycated protein assay kit of the present invention comprises a reaction solution containing the polymer of the present invention as a catalyst in an amount sufficient for at least one assay. The polymer of the present invention may be synthesized from vinylimidazole and vinylboronic acid using EGDMA as a crosslinking agent in the presence of fructosylvaline. Typically, the assay kit may comprise the polymer, a buffer solution adjusted to pH of 6.0 to 10, an appropriate mediator, a standard solution of fructosylvaline or its derivative for the preparation of a calibration curve, and directions for use. The glycated protein assay kit according to the present invention can be supplied in various forms such as a freeze-dried reagent and a solution in a suitable preservation medium.

In yet another aspect, the present invention provides an HbA1c assay kit. HbA1c can be assayed by enzymatically or chemically decomposing HbA1c to generate fructosylvaline, and quantifying the resulting fructosylvaline using the fructosylvaline assay kit of the present invention. Accordingly, the HbA1c assay kit of the present invention further comprises a hydrolyzing reagent or a proteolytic enzyme in addition to the fructosylvaline assay kit described above.

Sensors

In another aspect, the present invention provides sensors for assaying glycated albumin, HbA1c and fructosylamines. In the assay using the sensor of the present invention, as substrate is oxidized by catalysis of one of the polymers of the present invention, a mediator is reduced and electrochemically oxidized on an electrode, whereby the concentration of the substrate can be determined based on the amount of current as an indicator. The polymer employed in the sensor of the present invention may be obtained by polymerizing vinylimidazole and vinylboronic acid using EGDMA as a crosslinking agent in the presence of fructosylvaline.

Figure 3:
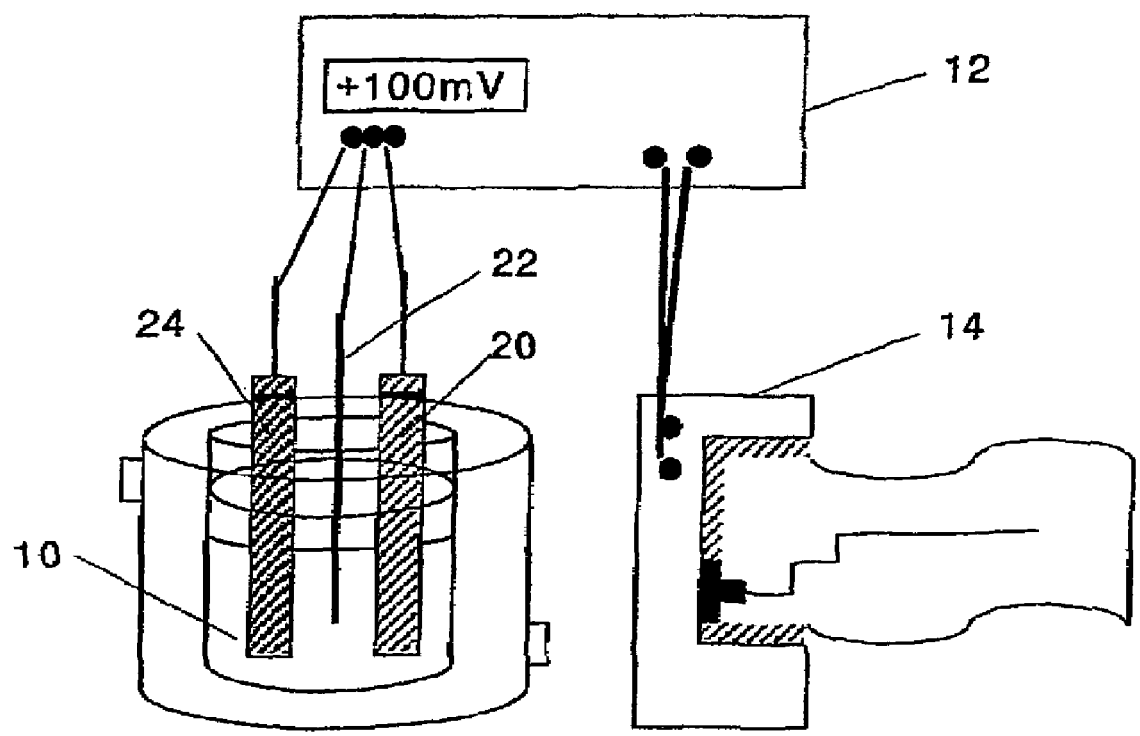
FIG. 3 is a diagram of a sensor system of the present invention.

According to the assay principle of the present invention, a sensor for fructosylamine assay can be constructed in the following manner. FIG. 3 shows an example of the sensor system of the present invention. For assays in an amperometric system, the sensor system includes a cell 10, a potentiostat 12 and a recorder 14, where the cell 10 contains an appropriate buffer, solution such as 10 mM potassium phosphate buffer (pH 7.0). The cell 10 may be of a batch system or a flow system. The cell 10 is provided with a working electrode 20, a counter electrode 22 and a reference electrode 24 disposed in the buffer solution. The potentiostat 12 applies a constant voltage (e.g., 100 mV) to the working electrode 20. As the working electrode 20, a carbon electrode, a gold electrode, or a platinum electrode may be used. The polymer of the present invention is immobilized on the working electrode 20. The polymer may be immobilized by using a crosslinking agent, encapsulating in a polymer matrix, covering with a dialysis membrane, or by using a photo-induced crosslinkable polymer, a conductive polymer or a redox polymer. These processes can also be used in combination.

For assaying fructosylamine in an amperometric system using a carbon, gold or platinum electrode, a polymer capable of binding to fructosylamine and catalyzing its oxidation in the presence of an electron acceptor is immobilized on the electrode to provide a working electrode 20, then the working electrode 20, a counter electrode 22 (e.g., a platinum electrode) and a reference electrode 24 (e.g., a Ag/AgCl electrode) are disposed in the cell 10 containing a buffer solution and an mediator held at a constant temperature. A predetermined voltage is applied to the working electrode 20 by the potentiostat 12. A sample is added to the system, and increase in current is monitored and recorded on the recorder 14. Such mediators include, for example, potassium ferricyanide, ferrocene, osmium derivatives and phenazine methosulfate.

In addition, an immobilized electron mediator can be used in the assay in the amperometric system with a carbon electrode, gold or platinum electrode. Specifically, both the polymer of the present invention capable of binding to fructosylamine and catalyzing its oxidation in the presence of an electron acceptor and an electron mediator may be immobilized on a polymer matrix on the electrode by adsorption or covalent binding to provide a working electrode 20. The electron mediator includes, for example, potassium ferricyanide, ferrocene, osmium derivatives and phenazine methosulfate. The working electrode 20, a counter electrode 22 (e.g., a platinum electrode) and a reference electrode 24 (e.g., a Ag/AgCl electrode) are disposed in the cell 10 containing a buffer solution held at a constant temperature. A predetermined voltage is applied to the working electrode 20 by the potentiostat 12. A sample is added to the system, and increase in current is monitored and recorded on the recorder 14.

In any of these systems, the fructosylvaline concentration in the sample can be determined based on a calibration curve obtained by using fructosylvaline standard solutions.

For HbA1c assay, a composite sensor is assembled by combining fructosylvaline assay sensor with, for example, a proteolytic enzyme (e.g., a protease) immobilized on a membrane. Structures of such a composite sensor involving a series of reactions by the action of a plurality of enzymes are well known in the art and are described in, for example, Biosensors—Fundamental and Applications—Anthony P. F. Tuner, Isao Karube and Geroge S. Wilson, Oxford University Press 1987.

All patents and publications cited herein are hereby incorporated by reference. In addition, the entire disclosure of Japanese Patent Application No. 2000-318618 to which the present patent application claims priority is also hereby incorporated by reference.

The present invention will be illustrated in further detail with reference to several examples below, which are not intended to limit the scope of the invention.

EXAMPLE 1

To a solution comprising 522 μl of methanol and 174 μl of water, 0.2 mmol of 4-vinylphenylboronic acid, 2 mmol of ethylene glycol dimethacrylate (EGDMA) as a crosslinking reagent, 0.06 mmol of 2,2'-azobisisobutyronitrile as a polymerization initiator, and 0.2 mmol of fructosylvaline as a template molecule were added. The polymerization reaction was allowed for proceed under Ar gas at 45° C. for 12 hours. The resulting polymer is hereinafter referred to as B-MIP. The polymer was ground in a mortar and sieved to prepare a polymer having a particle size of 40 μm. A control polymer B-CP was prepared in the same manner as above, except that fructosylvaline as the template molecule was not added. These polymers were washed twice with methanol-acetic acid (7:2), twice with acetonitrile-acetic acid (9:1), once with acetonitrile, and then once with methanol.

EXAMPLE 2

To the polymers obtained in Example 1 and suspended in 10 mM phosphate buffer solution (pH 7.0) to a concentration of 5 mg/ml, an appropriate amount of fructosylvaline was added, and the ability of the polymers to bind to fructosylvaline was determined. The results are shown in FIG. 1. The polymer B-MIP obtained by polymerization in the presence of fructosylvaline as a template molecule showed a binding constant and a maximum binding capability per unit polymer with fructosylvaline of 1.2 times and 2.1 times higher than the control B-CP, respectively.

EXAMPLE 3

To a solution comprising 522 μl of methanol and 174 μl of water, 1.6 mmol of 1-vinylimidazole, 0.8 mmol of 4-vinylphenylboronic acid, 2 mmol of ethylene glycol dimethacrylate (EGDMA) as a crosslinking reagent, 0.06 mmol of 2,2'-azobisisobutyronitrile as a polymerization initiator, and 0.2 mmol of fructosylvaline as a template molecule were added. The polymerization reaction was allowed to proceed under Ar gas at 45° C. for 12 hours. The resulting polymer is hereinafter referred to as BI-MIP. The polymer was ground in a mortar and sieved to prepare a polymer having a particle size of 40 μm. A control polymer BI-CP was prepared in the same manner as above, except that fructosylvaline as the template molecule was not added. These polymers were washed twice with methanol-acetic acid (7:2), twice with acetonitrile-acetic acid (9:1), once with acetonitrile, and then once with methanol.

EXAMPLE 4

Figure 2:
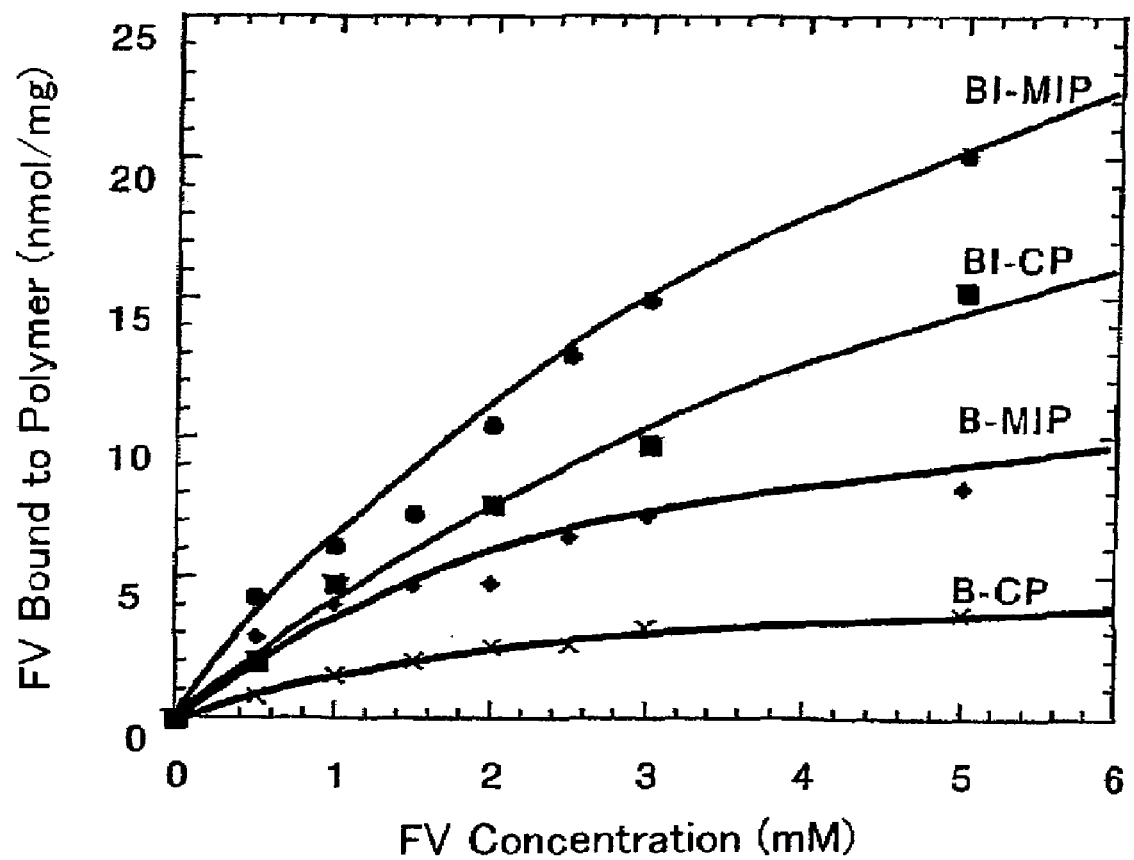
FIG. 2 shows the ability of the polymer synthesized in Examples 1 and 3 to bind to fructosylvaline; BI-MIP represents a vinylimidazole-boronic acid copolymer prepared in the presence of a template molecule; BI-CP represents a vinylimidazole-boronic acid copolymer prepared in the absence of a template molecule; B-MIP represents a boronic acid polymer prepared in the presence of a template molecule; and B-CP represents a boronic acid polymer prepared in the absence of a template molecule.

To the polymers obtained in Example 3 and suspended in 10 mM phosphate buffer solution (pH 7.0) to a concentration of 5 mg/ml, an appropriate amount of fructosylvaline was added and the ability of the polymers to bind to fructosylvaline was determined. The results are shown in FIG. 2. BI-MIP obtained by polymerization in the presence of fructosylvaline as a template molecule showed a binding constant and a maximum binding capability per unit polymer with fructosylvaline of 1.5 times and 1.6 times higher than the control BI-CP, respectively.

EXAMPLE 5

Figure 4:
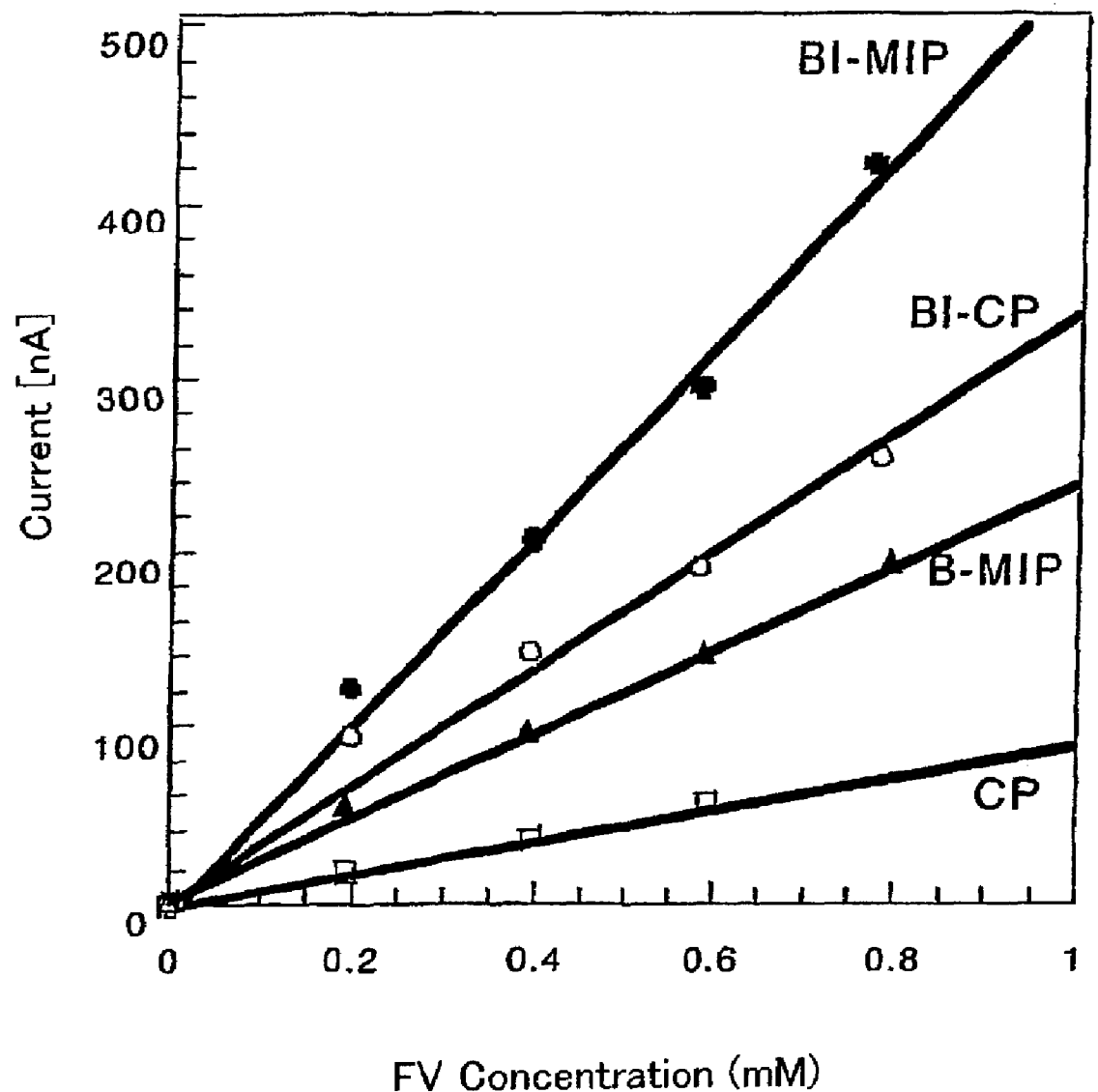
FIG. 4 shows a result of the assay in which the concentration of fructosylvaline is electrochemically determined using sensors prepared in Example 5; BI-MIP, BI-CP, B-MIP, and CP represent responses of the electrodes comprising a vinylimidazole-boronic acid copolymer prepared in the presence of a template molecule, a vinylimidazole-boronic acid copolymer prepared in the absence of a template molecule, a boronic acid polymer prepared in the presence of a template molecule, and a carbon paste electrode as a control, respectively.

To 50 mg of carbon paste was added 20 mg of each of the polymers prepared in Examples 1 and 3, and the mixture was charged into a carbon paste electrode. The resulting electrode was disposed in a solution of 10 mM phosphate buffer saline (pH 7.4) containing 1 mM 1-methoxyphenazine methosulfate (m-PMS). A voltage of 100 mV (vs. Ag/AgCl) was applied, then fructosylvaline as a substrate was added to the solution, and the response was monitored. The sensor system is illustrated in FIG. 3. Fructosylvaline was assayed using the sensor, and the result is shown in FIG. 4. A carbon paste electrode without any immobilized polymer showed very low response. In contrast, the electrode to which B-MIP or B-CP was immobilized exhibited a response of 2.5 times higher than the carbon paste electrode. The electrode to which BI-CP was immobilized exhibited a response of 3 times higher than the carbon paste electrode. The electrode to which BI-MIP was immobilized exhibited a response of 5 times higher than the carbon paste electrode.

EXAMPLE 6

The selectivity toward fructosylvaline of a polymer prepared in the presence of fructosylvaline as a template was investigated. Specifically, 10 mM phosphate buffer solution (pH 7.5) was placed in a thermostatic cell, and methoxy-PMS (m-PMS) in a final concentration of 1 mM was added thereto to a total volume of 10 ml. The carbon paste electrode prepared in Example 5 was used as a working electrode, and a platinum electrode and a Ag/AgCl electrode were used as a counter electrode and a reference electrode, respectively.

Figure 5:
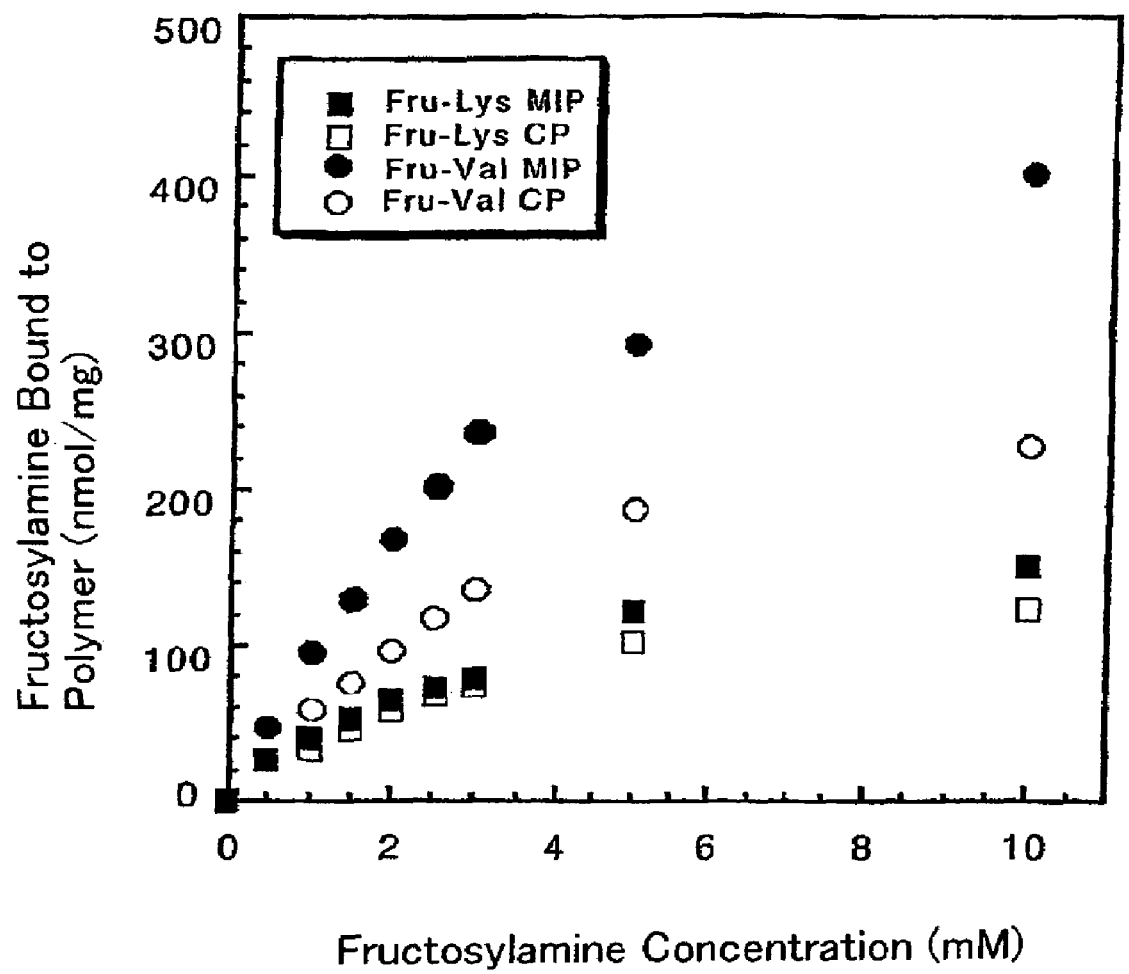
FIG. 5 is a diagram showing the selectivity of the polymers prepared in the presence of fructosylvaline as a template toward fructosylvaline as compared with $\epsilon$-fructosyl-lysine; Fru-Lys represents $\epsilon$-fructosyl-lysine; Fru-Val represents fructosylvaline; MIP represents a polymer prepared in the presence of fructosylvaline as a template; and CP represents a control polymer prepared in the absence of a template.
Figure 6:
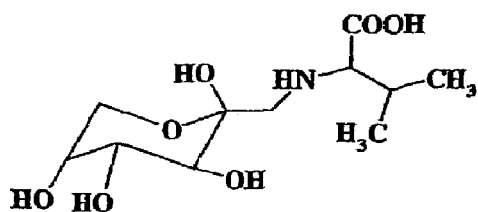
FIG. 6 is a table showing the selectivity of the polymer prepared in the presence of fructosylvaline as a template toward fructosylvaline as compared with fructosylamines; MIP represents a response of the electrode comprising a polymer prepared in the presence of fructosylvaline as a template; and CP represents a response of the electrode comprising a control polymer prepared in the absence of a template.
Figure 6:
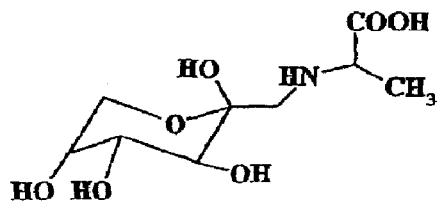
Figure 6:
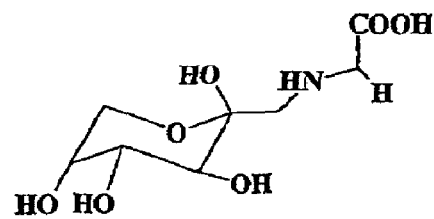
Figure 6:
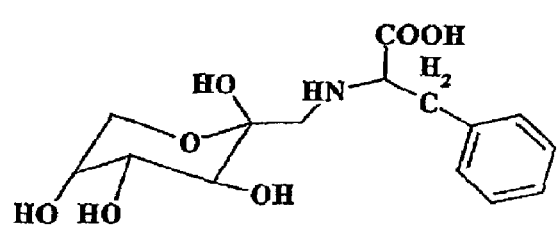
Figure 6:
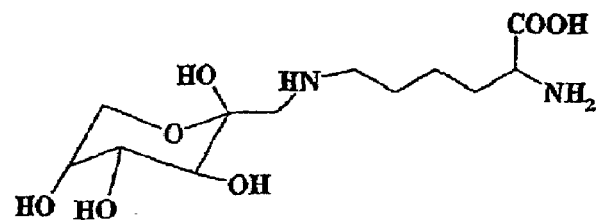

A voltage of +100 mV was applied. When the current became constant, an appropriate concentration of fructosylvaline was added to the cell and increase in current was monitored. The same procedure was performed with fructosylglycine, fructosylalanine, fructosyl phenylalanine, and ε-fructosyllysine. In this procedure, the initial current before addition of fructosylvaline was set at 0 A, and the assay was performed at 40° C. The results are shown in FIGS. 5 and 6, indicating that the electrodes exhibited increased reactivity with all of the fructosylamine compounds tested. The difference between the imprinted polymer and the control polymer was highest for fructosylglycine and lower for fructosylvaline, fructosyl-alanine, fructosyl-phenylalanine, and fructosyl-lysine in this order.

EXAMPLE 7

Effects of addition of various basic monomers were investigated. To a mixture of 1-vinylimidazole, 4-vinylphenylboronic acid, a basic monomer selected from allylamine, N,N'-dimethylaminoethyl methacrylate, dimethylaminopropyl methacrylate and diethylaminoethyl methacrylate, and ethylene glycol dimethacrylate as a crosslinking agent (8:4:8:10) dissolved in a solvent mixture of methanol and water (4:1), a polymerization initiator ABDV was added. The polymerization reaction was allowed to proceed under Ar gas at 45° C. for 12 hours. The resulting polymer was crushed to a particle size of 32 μm or less, and washed and dried.

To 50 mg of carbon paste, 20 mg of each of the above-obtained polymers and 20 μl of mineral oil were added and thoroughly mixed. The resulting mixture was charged into a carbon paste electrode to prepare a working electrode. Fructosylvaline or fructosyl-lysine was added to a reaction system comprising the working electrode, an Ag/AgCl electrode as a reference electrode, a platinum electrode as a counter electrode in a reaction solution containing 10 mM ppb (pH 7.5) and 1 mM m-PMS, and increase in current was monitored at a temperature of 40° C. at a voltage of +100 mV/AgCl.

Figure 7:
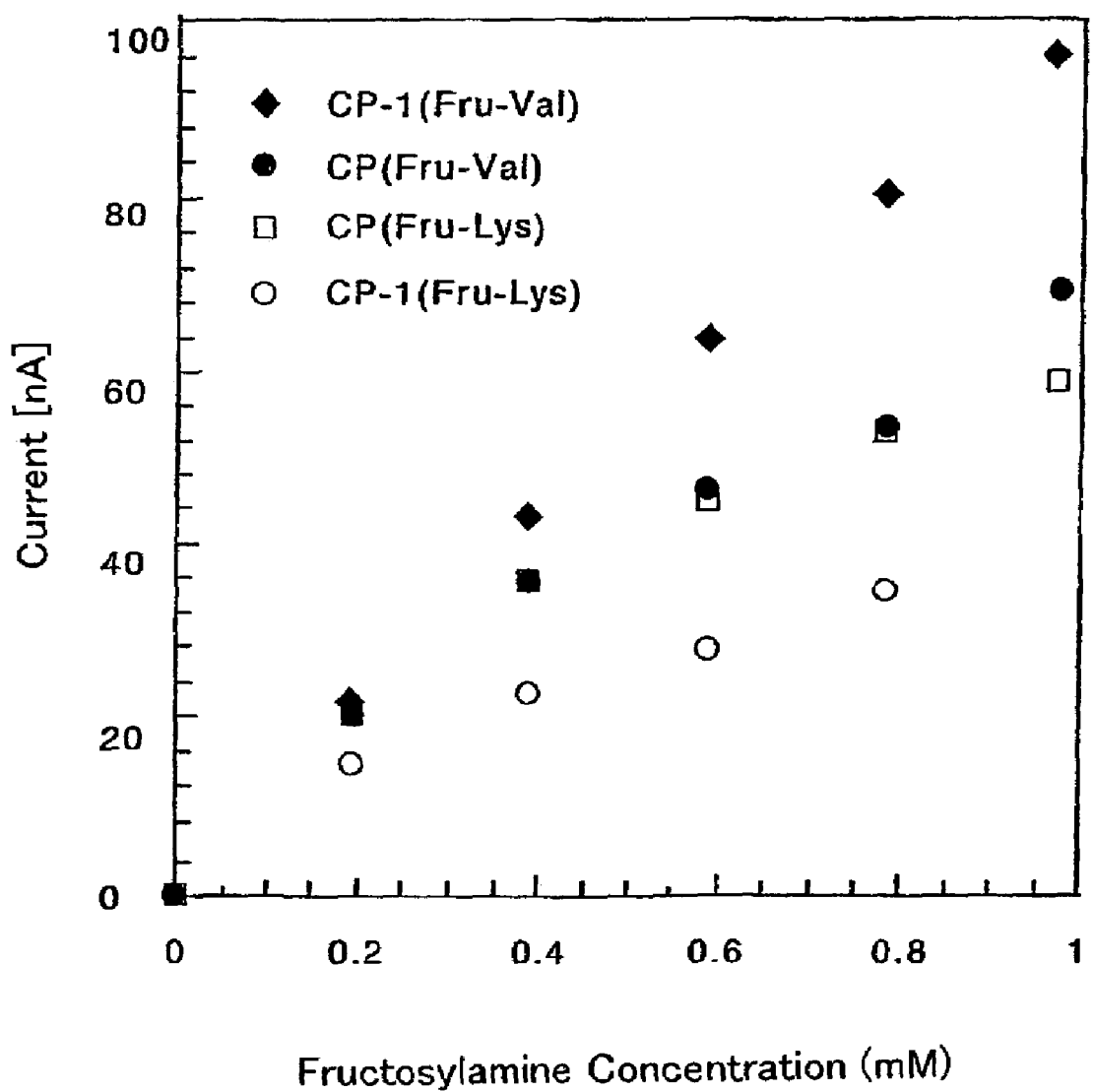
FIG. 7 shows a response of the electrode comprising a copolymer prepared in the presence of allylamine as a basic monomer to fructosylvaline and fructosyl-lysine; CP-1 represents a response of the electrode comprising a copolymer prepared in the presence of allylamine; and CP represents a response of a control carbon paste electrode.

The electrode to which allylamine was immobilized exhibited higher response to fructosylvaline and lower response to fructosyl-lysine compared to the electrode comprising carbon paste alone (FIG. 7). The electrode to which N,N'-dimethylaminoethyl methacrylate or dimethylaminopropyl methacrylate was immobilized exhibited equal response to fructosylvaline and lower response to fructosyl-lysine compared to the electrode comprising carbon paste alone. The electrode to which diethylaminoethyl methacrylate was immobilized exhibited lower response to fructosylvaline and fructosyllysine compared to the electrode comprising carbon paste alone. In this case, the response to fructosylvaline was higher than that to fructosyl-lysine.

These results show that, by adding basic monomers in the polymerization reaction, the resulting polymers have improved selectivity toward fructosylvaline over fructosyllysine even if the polymers are prepared in the absence of fructosylvaline as a template.

EXAMPLE 8

Figure 8:
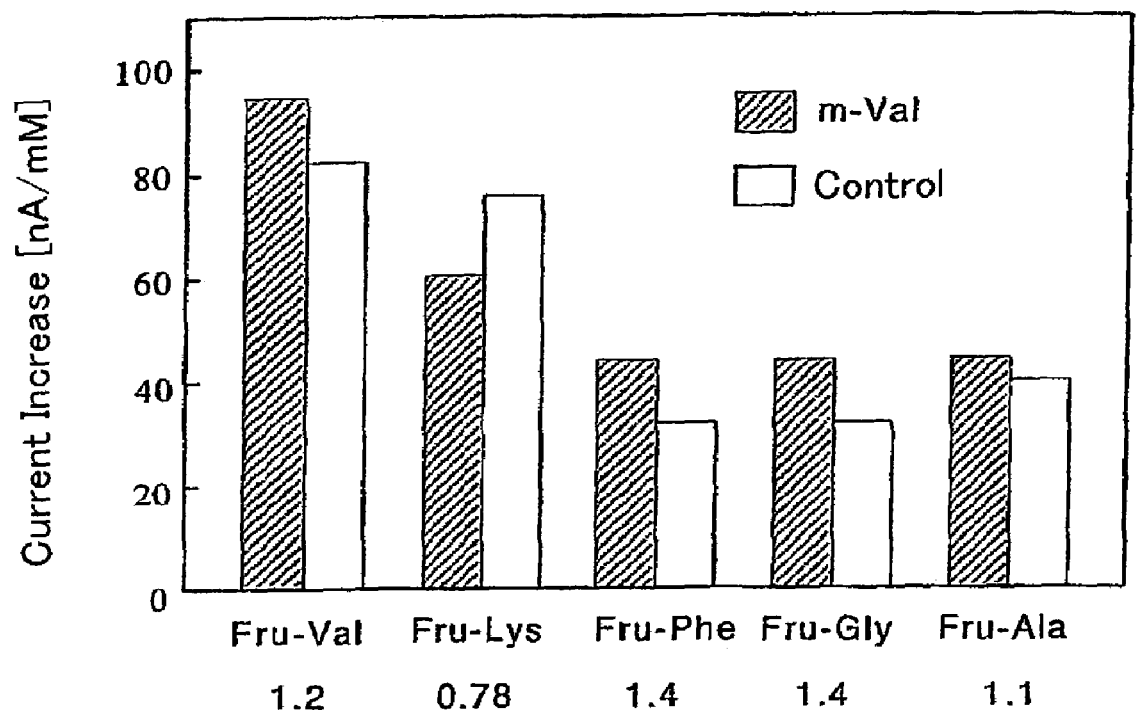
FIG. 8 shows a response of the electrode comprising a polymer synthesized in the presence of methylvaline as a template to various fructosylamines; m-Val represents a polymer synthesized in the presence of methylvaline as a template; Control represents a polymer synthesized in the absence of a template; numerical values indicated beneath the compounds represent the ratios of current increase of m-Val vs control.

A polymer was synthesized in the same manner as in Example 3, except that methylvaline was used as the template in place of fructosylvaline. A sensor was prepared by immobilizing the polymer on a carbon paste electrode, and the response of the electrode to fructosylamine were monitored in the same manner as in Example 5. As a control, a polymer synthesized in the absence of a template was used. The results are shown in FIG. 8, indicating that the polymer prepared in the presence of methylvaline as a template has improved response to alpha-glycated fructosylamine and has higher selectivity for fructosylvaline over ε-fructosyl-lysine, as with the polymer prepared in the presence of fructosylvaline as a template.

EXAMPLE 9

Polymers were prepared in the same manner as in Example 3, except that 4(5)-vinylimidazole or 4-vinylimidazole was used in place of 1-vinylimidazole. These polymers were immobilized on electrodes, and the responses of the electrodes to fructosylvaline and fructosyl-lysine were monitored. All of the polymers were capable of catalyzing oxidation of fructosylvaline, and had equal response to fructosylvaline and fructosyllysine. However, unlike the polymer prepared by using 1-vinylimidazole, they showed no selectivity toward fructosylvaline.

INDUSTRIAL APPLICABILITY

The synthetic polymer of the present invention has a catalytic activity which mimics enzymatic reactions. The polymer is useful in assay of glycated proteins such as glycated hemoglobin (HbA1c) and glycated albumin, as well as the decomposition product fructosylamine, such as fructosylvaline.

The invention claimed is:

1. A method for preparing a synthetic polymer which is capable of binding to fructosylamine and catalyzing oxidation of the fructosylamine in the presence of an electron acceptor, said method comprising
    copolymerizing a vinylimidazole and a vinylboronic acid in the presence of a template molecule selected from the group consisting of fructosylamine and methylamine.

2. The method according to claim 1, wherein the vinylimidazole is 1-vinylimidazole.

* * * * *